United States Patent
Rigaux (10) Patent No.: US 11,864,898 B2
(45) Date of Patent: Jan. 9, 2024

(54) MUSCLE FATIGUE DETERMINATION METHOD AND SYSTEM

(71) Applicant: MYOCENE, Liège (BE)

(72) Inventor: Pierre Rigaux, Liège (BE)

(73) Assignee: MYOCENE, Liège (BE)

( * ) Notice: Subject to any disclaimer, the term of this patent is extended or adjusted under 35 U.S.C. 154(b) by 610 days.

(21) Appl. No.: 17/091,468

(22) Filed: Nov. 6, 2020

(65) Prior Publication Data

US 2022/0142537 A1 May 12, 2022

(51) Int. Cl.
*A61B 5/22* (2006.01)
*A61B 5/00* (2006.01)

(52) U.S. Cl.
CPC ............ *A61B 5/224* (2013.01); *A61B 5/6891* (2013.01); *A61B 5/70* (2013.01); *A61B 5/7455* (2013.01); *A61B 2562/0261* (2013.01)

(58) Field of Classification Search
CPC ... A63B 21/4034; A61B 5/224; A61B 5/6891; A61B 5/70; A61B 5/7455; A61B 2562/0261; A61B 5/05; A61B 5/6828
USPC ........................................................ 600/595
See application file for complete search history.

(56) References Cited

U.S. PATENT DOCUMENTS

| | | |
|---|---|---|
| 5,070,873 A | 12/1991 | Graupe et al. |
| 9,114,255 B1 | 8/2015 | Hartman et al. |
| 2005/0283205 A1 | 12/2005 | Lee et al. |
| 2017/0347941 A1 | 12/2017 | Ejiri et al. |

FOREIGN PATENT DOCUMENTS

| | | | |
|---|---|---|---|
| CN | 103691059 A | 4/2014 | |
| CN | 107468255 A | 12/2017 | |
| CN | 110522999 A | 12/2019 | |
| CZ | 2018559 A3 * | 3/2020 | ............... A61B 5/22 |
| JP | 2003169782 A * | 6/2003 | |
| JP | 5916154 B2 | 5/2016 | |
| KR | 101685013 B1 | 12/2016 | |
| WO | 1990/006152 A1 | 6/1990 | |
| WO | 2002/013696 A1 | 2/2002 | |
| WO | 2020/078486 A1 | 4/2020 | |

OTHER PUBLICATIONS

Silva, M. T., Pereira, A. F., Martins, J. M., & Biomechatronics Research Group. (2011). An efficient muscle fatigue model for forward and inverse dynamic analysis of human movements. Procedia IUTAM, 2, 262-274. (Year: 2011).*

Kirsch, N. A. (2016). Control methods for compensation and inhibition of muscle fatigue in neuroprosthetic devices (Doctoral dissertation, University of Pittsburgh). (Year: 2016).*

(Continued)

*Primary Examiner* — Daniel L Cerioni
*Assistant Examiner* — Jonathan E. Cooper
(74) *Attorney, Agent, or Firm* — CHRISTENSEN O'CONNOR JOHNSON KINDNESS PLLC (57) ABSTRACT

A method for determining a muscle fatigue of a muscle includes a first step of electrostimulating the muscle at different frequencies. A second step of the method includes determining forces developed by the muscle in response to the electrostimulations of the first step. A third step includes determining a muscle fatigue on basis of the forces determined in the second step.

14 Claims, 2 Drawing Sheets

(56) References Cited

OTHER PUBLICATIONS

Zhang, D., Ren, Y., Gui, K., Jia, J., & Xu, W. (2017). Cooperative control for a hybrid rehabilitation system combining functional electrical stimulation and robotic exoskeleton. Frontiers in Neuroscience (Year: 2017).*

Chiu, Loren Z.F. et al., "The Fitness-Fatigue Model Revisited: Implications for Planning Short- and Long-Term Training," Strength and Conditioning Journal, Dec. 2003, pp. 42-51, vol. 25, No. 6, National Strength & Conditioning Association.

International Search Report and Written Opinion dated Aug. 16, 2022, issued in corresponding International Application No. PCT/EP2022/061932, filed May 4, 2022, 16 pages.

Douma, K. W. et al.; "Reliability of the Q Force; a mobile instrument for measuring isometric quadriceps muscle strength"; BMC Sports Science, Medicine and Rehabilitation; 2016; pp. 1-12; vol. 8, No. 4.

Edwards, R. H. T. et al.; "Fatigue of Long Duration in Human Skeletal Muscle After Exercise"; Journal of Physiology; Mar. 23, 1977; pp. 769-778; vol. 272.

Ruggiero, Luca et al.; "Prolonged low-frequency force depression is underestimated when assessed with doublets compared with tetani in the dorsiflexors"; Journal of Applied Physiology; Mar. 14, 2019; pp. 1352-1359; vol. 126; American Physiological Society.

Verkerke, G. J. et al.; "Precision, comfort and mechanical performance of the Quadriso-tester, a quadriceps force measuring device"; Medical & Biological Engineering & Computing; May 2003; pp. 283-289; vol. 41.

Martin, V.; "Assessment of low-frequency fatigue with two methods of electrical stimulation"; Journal of Applied Physiology; Jul. 11, 2004; pp. 1923-1929; vol. 97; American Physiological Society.

* cited by examiner

MUSCLE FATIGUE DETERMINATION METHOD AND SYSTEM

BACKGROUND

The disclosed subject matter relates to a muscle fatigue determination method and to a system for implementing this method.

Animal activities, in particular human activities, induce "fatigue". Such fatigue can be nervous (i.e. induced by intellectual or psychic activities) or physical (i.e. induced by physical work). A physical fatigue is also called a "muscle fatigue" because it results from a muscular work and leads to a decrease in the force that can be provided by the affected muscle(s). In particular, muscle fatigue can result in an incapacity to maintain and/or repeat a physical effort. As a consequence, the identification, measurement and/or monitoring of muscle fatigue play an important role, for example, in sport practices (e.g. for the purpose of training effectiveness optimization, injury prevention, individual sport training program conception, muscle readiness, . . . ), or in physiotherapy for muscle rehabilitation (e.g. for the purpose of exercise monitoring, treatment optimization, excessive treatment prevention, . . . ), and more generally in medicine.

A known method for assessing muscle fatigue of a subject is to perform a test requiring maximum voluntary contraction of said muscle (e.g. by voluntary movements), repeated several times. A muscle fatigue is deemed to have been identified if a predetermined maximal muscular force corresponding to a monitored data (time, speed, force, power, acceleration, . . . ) cannot be reached. The motivation of the subject for reaching a maximum contraction can however affect such muscle fatigue evaluation. Moreover, as this test induces itself an important muscle fatigue, it affects itself the results obtained by the method: it cannot be reproduced several times typically, and it cannot be performed after an intense muscle work (e.g. after a sport competition). In addition, this method has the drawback to put the subject at risk of injury. It is then desirable to develop an improved muscle fatigue determination method.

SUMMARY

A first object of the disclosed subject matter is to provide a more efficient, safe and flexible method for determining a muscle fatigue. In particular, an object of the disclosed subject matter is to provide a method allowing the determination of a muscle fatigue without inducing itself muscle fatigue, independently of the subject will, at any time, without putting the subject at risk of injury.

For this purpose, the disclosed subject matter provides a determination method of a muscle fatigue of a muscle, comprising the following steps:
 (i) electrostimulating the muscle at different frequencies;
 (ii) determining forces developed by the muscle in response to the electrostimulations of step (i); and
 (iii) determining a muscle fatigue on basis of the forces determined at step (ii).

The method according to the disclosed subject matter is more efficient, safe and flexible for determining the muscle fatigue than the method described in the prior art. In fact, the use of electrostimulations at steps (i) allows to stimulate the muscle whatever its fatigue and to make the muscle developing an involuntary force in response to the electrostimulations. This step can then be performed at any time, also after a sport training, without putting the subject at risk of injury, and it is not dependent on the subject will to urge a maximal contraction of the muscle. This step (i) also does not induce muscle fatigue given that the number of electrostimulations (and frequencies) are preferably limited and naturally performed shortly, in order to observe muscle reactions and to determine the forces at step (ii). The muscle fatigue before and after an execution of the determination method is advantageously substantially the same. This determination method allows to determine the muscle fatigue efficiently. Indeed, the inventors noticed that, as muscle fatigue deforms non-uniformly the curve of the force developed by the muscle in response to an electrostimulation at a frequency as a function of this frequency, it was possible to determine the muscle fatigue at step (iii) on basis of a determination of this force for different frequencies, for example, by comparing muscle developed forces. This has the major advantage to be independent from the context of execution of the determination method. In particular, no comparison to a such standard known curve at rest for the subject, no preliminary measures, and no specific execution conditions are needed.

The determination method according to the disclosed subject matter is convenient for a wide range of applications, in particular for determining muscle fatigue of sport professionals before, during or after a training or a competition, as well as muscle fatigue of injured or elderly people during muscle rehabilitation.

Another advantage of the determination method of the disclosed subject matter is that it allows for a determination of specific muscle fatigues. Indeed, the muscle fatigue depends on many physiologic factors. In particular, the muscle fatigue can be caused by a deficiency of a neuromuscular neurological control when the latter cannot stimulate the muscle fibers to a maximum potential (leading to a so-called "central muscle fatigue"), or by alteration of the contraction force at direct level of the muscle fibers (leading to a so-called "peripheral muscle fatigue"). In the framework of the disclosed subject matter, the determination method allows to determine directly at step (iii) the peripheral muscle fatigue given that the electrostimulations of step (i) affect directly of the peripheral muscle fibers, independently from the central neurological control of the muscle contraction. Step (iii) can nevertheless optionally also comprise a central muscle fatigue determination substep by subtraction of the determined peripheral muscle fatigue from another global fatigue measurement. This distinctive muscle fatigue determination is new with regard to the prior art methods.

Moreover, the peripheral muscle fatigue comprises itself two kinds of muscle fatigues depending how long the muscle fatigue affects the muscle: the so-called "short-lasting peripheral muscle fatigue" that is essentially linked to energetic and/or metabolic factors, from which it can be recovered quickly (some minutes), and the so-called "long-lasting peripheral muscle fatigue" that persists for several hours and even several days (e.g. after a physical effort). The peripheral muscle fatigue determined at step (iii) is preferably and more specifically a long-lasting peripheral muscle fatigue. Optionally, a short-lasting peripheral muscle fatigue can also be determined at step (iii) by additional determination of the muscle fatigue in an interval of time following the method of the disclosed subject matter, and subtraction of the obtained results.

In the framework of the disclosed subject matter, the term "electrostimulation" and any of its variants preferably refer to neuromuscular electrical stimulation or any kind of stimulation of the motor neurons of the tested muscle. Such stimulation is preferably performed by a stimulator comprising a generator of electric pulses and electrodes adapted for being placed on the skin of the subject, at proximity and/or beside the muscle, and connected to the generator in such a way that a current can be transmitted to the muscle by the electrodes. The intensity and the frequency of the electric pulses can be adjusted. Such generator and electrodes are well known by a skilled person.

Preferably, the frequencies are comprised between 0 and 1000 Hz, more preferably smaller than 500 Hz, more preferably, smaller than 200 Hz. The frequencies can be comprised between 5 and 150 Hz. Such bounds allow to avoid muscle fatigue induction by an execution of the determination method.

In the framework of the present disclosure, the use of the indefinite article "a", "an" or the definite article "the" to introduce an element does not exclude the presence of a plurality of these elements. In this document, the terms "first", "second", "third" and the like are solely used to differentiate elements and do not imply any order in these elements. In this document, the terms "at level of" and "at the level of" are used equivalently. In the framework of this document, the terms "on basis of" and "on the basis of" are used equivalently. The latter are not limitative: the fact that a first quantity is determined on basis of a second quantity do not exclude that the first quantity can also be determined on basis a third quantity together with the first quantity.

In the framework of the present disclosure, the terms "smaller than" and "greater than" are to be interpreted as the mathematical symbols "≤" and "≥" respectively. The use of the verbs "comprise", "include", "involve" or any other similar variant, as well as their conjugational forms, cannot exclude the presence of elements other than those mentioned. When the verb "comprise" is used for defining an interval by the terms "comprised between" two values, these two values should not be interpreted as excluded from the interval.

Figure 2:
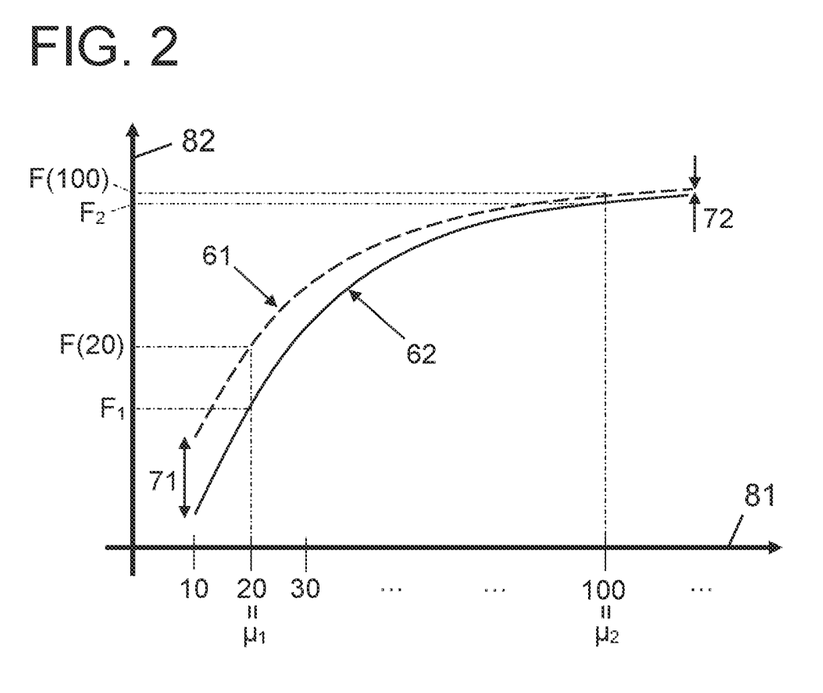
FIG. 2 shows curves of the force developed by a muscle in response to an electrostimulation at a given frequency as a function of this frequency.

According to an embodiment of the determination method according to the disclosed subject matter, the frequencies comprise:

a first frequency, and a second frequency greater than the first frequency, the first frequency differing from at least 10% of the second frequency (in the sense that: if $\mu_1$ and $\mu_2$ are the first and second frequencies, $\mu_2-\mu_1 \geq \mu_2/10$). These first and second frequencies can satisfy one of the previously recited frequency ranges. In this case the forces determined at step (ii) comprises a first force developed by the muscle in response to the electrostimulation of step (i) at the first frequency, and a second force developed by the muscle in response to the electrostimulation of step (i) at the second frequency. The difference of at least 10% between the first and second frequencies is advantageous in order to ensure that at least two points (frequency used at step (i), force determined at step (ii)) on the curve (of the force developed by the muscle in response to an electrostimulation at a frequency as a function of this frequency) are sufficiently spaced one from the other for performing more efficiently step (iii). This allows to take all advantage of a non-uniformity and non-linearity of the deformation of the curve in function of a preexisting muscle fatigue given that the forces developed by the muscle in response to electrostimulations at low frequencies, e.g. between 0 to 50 Hz, is more affected by this muscle fatigue than the forces developed by the muscle in response to electrostimulations at higher frequencies, as illustrated in FIG. 2 hereafter introduced. In particular, the above-mentioned difference is preferably at least 20%, more preferably at least 50%. Preferably, the first frequency is comprised between 0 and 50 Hz and/or the second frequency is comprised between 50 and 200 Hz. Preferably, the first frequency is about 20 Hz and/or the second frequency is about 100 Hz. Any other similar couple of values for the first and second frequencies can be used, for example: 10 and 50 Hz, 30 and 80 Hz, 50 and 150 Hz, etc.

More preferably, according to the above-mentioned embodiment, the different frequencies of step (i) consist in the first and second frequencies and the forces determined at step (ii) consist in the first and second forces. Advantageously, it is possible to determine the muscle fatigue at step (iii) only by considering these two forces. It will be explained hereafter. The advantage is to avoid muscle fatigue induction by limiting the electrostimulations at step (i) in number and frequency. Another advantage is to facilitate the execution of step (iii) by considering only a limited number of data. The disclosed subject matter however is not limited to different frequencies consisting in only the first and second frequencies. Other numbers than two frequencies can be considered. As an example, the different frequencies (and associated forces determined at step (ii) can be three, four, five, six, seven, eight, nine, ten or more frequencies, and those can also be equidistant in a range of frequency, such that those defined in the previously described ranges.

Preferably, step (iii) comprises a computation of a ratio of the first force to the second force, the muscle fatigue being determined on basis of this ratio. More specifically and preferably, step (iii) also comprises a comparison of the computed ratio to a threshold, and a determination of the muscle fatigue based on this comparison of the computed ratio to the threshold. This implementation of step (iii) is very simple and allows a fast and low complexity computation for determining the muscle fatigue. It is also very efficient. Indeed, as previously explained, as the first frequency differs from at least 10% of the second frequency, the ratio is fully affected by the non-uniformity of the curve deformation in function of the muscle fatigue. As a consequence, when the above-mentioned comparison allows to identify a difference between the computed ratio and a threshold corresponding to an expected ratio for a non-fatigued muscle, such difference expresses a muscle fatigue that can then be determined at least implicitly and preferably explicitly.

This embodiment of the disclosed subject matter, and the term "on basis of" does not exclude a step (iii) that would also take into account other information or computations derived from the forces determined at step (ii). For example, at least another computation on other forces determined at step (ii) can be used for determining the muscle fatigue, and step (iii) can comprise a substep for averaging the muscle fatigue determined in this way, and by the comparison of the computed ratio to the threshold, which allow a more precise and efficient determination of the muscle fatigue as an average of such determinations. For example, this at least another computation can comprise a ratio computation of a third force to a fourth force among the forces determined at step (ii).

As a generalization of the preceding embodiments of the disclosed subject matter, step (iii) preferably comprises a comparison of the forces determined at step (ii), and a determination of the muscle fatigue based on this comparison of the forces.

The threshold consists preferably in a number $F(\mu)/F(\mu')$, where:

F is a human independent increasing regular function expressing a force developed by a non-fatigued muscle in response to an electrostimulation as a function of a frequency of this electrostimulation; and μ and μ' are respectively the first and the second frequencies.

In other words, in this case, F is preferably a skilled person known theoretical function, underlying a family of thresholds of the form F(μ)/F(μ') that can be used for defining the threshold. Expressing the ratio in this way is advantageous because it is human independent and indirectly given through the function F for any couple of the first and second frequencies. This embodiment is not limitative of the scope of the disclosed subject matter. It is not necessary to consider a whole function F for the abovementioned embodiment involving only the first and the second frequencies, as a number corresponding to these frequencies is sufficient.

In the context of some embodiments:
the first frequency is preferably comprised between 10 and 40 Hz; and/or
the second frequency is preferably comprised between 90 and 120 Hz.

In this case, the threshold is preferably comprised between 40 and 90%. More preferably, the first frequency is about 20 Hz, the second frequency is about 100 Hz, and the threshold is about 60%, or 65%, or 70%, or 75%, or 80%. Such a combination of values makes it very easy and efficient to implement the determination method of the disclosed subject matter as it was previously explained. It does obviously not limit the scope of the disclosed subject matter, and other values can be considered.

In the framework of the present document, the terms "determining", "determine", "determination" and any other variants correspond preferably to the terms "quantifying", "quantify" and "quantification" in the sense that the muscle fatigue is preferably not just identified but explicitly measured and/or computed. For example, in the preceding embodiments, an explicit measure and/or computation can be derived from the comparison of the computed ratio to the threshold and/or from determined muscle fatigue averaging. The scope of step (iii) nevertheless preferably does not exclude a determination of the muscle fatigue based on other physical quantities at least partially derived from the forces determined at step (ii), such as, for instance, associated torques. Reciprocally, the scope of step (ii) preferably does not exclude a determination of the forces based on intermediate physical quantities related to the forces that can be measured in response to the electrostimulations of step (i), such as, for instance, displacements, accelerations, and/or torques.

According to other embodiment of the determination method of the disclosed subject matter, the frequencies comprise a minimal frequency smaller than 50 Hz, and a family of frequencies smaller than 200 Hz and integer multiple of the minimal frequency. This family comprises more preferably all the frequencies smaller than 150 Hz and integer multiple of the minimal frequency. In other words, in this case, the frequencies of this family are equidistant. Although this embodiment requires more electrostimulations at step (i), it is advantageous because it allows to acquire more data among which at least some underlie a wide variety of points (frequency used at step (i), force determined at step (ii)) at least locally, preferably globally, uniformly distributed on the curve mention (of the force developed by the muscle in response to an electrostimulation at a frequency as a function of this frequency) for performing efficiently and precisely step (iii). The family can for example consists in {5n Hz|1≤n≤30, n integer}={5 Hz, 10 Hz, 15 Hz, . . . , 150 Hz} for 5 Hz being the minimal frequency, or {30 Hz, 60 Hz, 90 Hz, 120 Hz} for 30 Hz being the minimal frequency. The family can also be for example {10 Hz, 20 Hz, 30 Hz, 100 Hz, 110 Hz, 120 Hz} for 10 Hz being the minimal frequency, all the frequencies integer multiple of 10 Hz being then not comprise within the family.

Preferably, according to the preceding embodiment of the method, step (iii) comprises:
a computation of a discrete integral of a (discrete) function associating, to each frequency of the family, a force determined at step (ii) developed by the muscle in response to the electrostimulation of step (i) at this frequency;
a determination of the muscle fatigue based on the computed discrete integral.

This discrete integral corresponds typically to a Riemann sum. It is preferably efficiently performed when the family comprises all the integer multiple of the minimal frequency smaller than 150 Hz, the latter being preferably smaller than 20 Hz, more preferably smaller than 10 Hz, for a good computation precision. In an embodiment, step (iii) comprises a comparison of the computed discrete integral to an area value, and a determination of the muscle fatigue based on this comparison of the computed discrete integral to the area value. This area value is preferably a value of the area under the previously discussed graph of the function F. As well known in discrete calculus, the comparison allows to evaluate a difference between this theoretical area for a non-fatigued muscle and its approximations by a Riemann sum for the muscle, and to determine the muscle fatigue on this basis in a precise way because of the number and preferred global uniform repartition of the frequencies of the family. Optionally, the different frequencies consist in this family of frequencies.

Some embodiments are compatible with various of the other preceding embodiments. In particular, it is possible to consider a muscle fatigue determination at step (iii) based on a computed ratio and on a computed discrete integral, for example by averaged comparison of these computed ratio and computed discrete integral to human independent expected normal values for a non-fatigued muscle. In this case, the first and second frequencies can also belong to the family.

According to another embodiment of the method of the disclosed subject matter fully compatible with the preceding embodiments, the forces are determined in steps (ii) by direct force measurements, preferably by means of a strain gauge or a dynamometer. In particular, the determination of the forces at step (ii) is done directly, by measuring forces (in Newton), by appropriate technologies and not by intermediate or indirect measures and/or observations (such as by electromyography) nor deduction or estimation inducing a risk of error in step (ii). These direct force measurements are preferably performed by a new and dedicated device introduced hereafter as part of a system of the disclosed subject matter.

Preferably, the muscle involved in the disclosed subject matter consists in a muscle of a lower limb of a human. Preferably, this muscle consists in the quadriceps or the hamstring. In any of these cases, according to an embodiment of the disclosed subject matter, the method comprises the following steps before step (i):
(a) providing a device comprising:
a seat for receiving the human in a seated position, and adapted for being positioned on a horizontal support;

a leg support element mechanically coupled to the seat, and adapted for receiving at least part of a leg of the lower limb;

an instrument for measuring the (above-mentioned) forces at level of the leg support element;

(b) positioning the seat on a horizontal support;

(c) positioning the human on the seat, in a seated position; and (d) positioning at least part of the leg on the leg support element.

Preferably, the forces are determined at step (ii) by means of this instrument. This device is advantageously very simple and easy to move, while allowing to determine precisely the forces at step (ii). The process for executing step (i) is also very simple as the human is seated on the seat, his leg being simply positioned and preferably maintained in the leg support element. Preferably, the weight of the human exerted at level of the seat allows simply the device to remain substantially stationary with respect to the horizontal support during an execution of steps (i) and (ii). In particular, no complex structure is needed for receiving the human and executing the method of the disclosed subject matter. A simple plane coupled to the leg support element can be used as seat and positioned on a horizontal support such as a table or another seat, anywhere. The device is fully detailed hereafter as part of a muscle fatigue determination system of the disclosed subject matter.

Preferably, above-mentioned steps (c) and (d) are such that:

a foot of the lower limb hangs in the air; and/or, preferably and, a whole thigh of the lower limb lies on the seat; and/or, preferably and, a back of a knee of the lower limb is in contact with a lateral side of the seat.

Advantageously, the seat is the only contact point of the lower limb (at a seat front surface level for the thigh and at a seat lateral surface level for the knee) which allows to know perfectly the measurement conditions of the forces at step (ii) and to avoid any measure perturbation that could be induced by a force exerted by the foot on a support, for instance on the ground. Preferably, the human is positioned at steps (b) and (c) such that its back is straight and form a substantially right angle with the lower limb thigh. Thanks to the simple structure of the device and the easy positioning of the human, the measures of the forces by the instrument are reproducible. This is very advantageous for the purpose of applications of the determination method of the disclosed subject matter given that muscle fatigue determined at step (iii) can be compared from one day to another, whenever and wherever, provided that the seat can be positioned on a horizontal support, without the necessity of executing the determination method in the same place and in the same conditions, and without taking care of a multiplicity of positioning parameters of the human.

A second object of the present disclosed subject matter is to provide an efficient, safe and flexible system for determining a muscle fatigue. In particular, it is to provide a system for implementing the determination method according to the first object of the disclosed subject matter, and then allowing to determine a muscle fatigue without inducing itself muscle fatigue, independently of the subject will, at any time, without putting the subject at risk of injury.

For this purpose, the disclosed subject matter provides a system for determining a muscle fatigue of a muscle, comprising:

an apparatus for generating an electrostimulation of the muscle at a range of frequencies, and comprising a controller for selecting any frequency of electrostimulation in the range of frequencies;

a device for determining a force developed by the muscle in response to an electrostimulation generated by the apparatus;

a logical unit connected to the device and configured for determining a muscle fatigue on basis of forces determined by the device as forces developed by the muscle in response to electrostimulations generated by the apparatus at different frequencies of the range of frequencies.

The system according to this second object of the disclosed subject matter allows for executing the determination method according to the first object of the disclosed subject matter. In particular, preferably step (i) is implemented by the apparatus, step (ii) is implemented by the device, and/or step (iii) is implemented by the logical unit. It can be notice that a logical unit is however optional in practice for implementing the determination method of the disclosed subject matter. For instance, an embodiment can be implemented at step (iii) more generally by mental calculus.

All the embodiments of the determination method according to the disclosed subject matter and the advantages of these embodiments apply mutatis mutandis to the present system according to the disclosed subject matter. In particular, this system is efficient, safe and flexible for determining the muscle fatigue as previously described.

Preferably, the range of frequencies extends at least on any of the interval of the previously mentioned frequencies. Preferably, it extends from 0 to 200 Hz. According to an embodiment of the system, the logical unit is configured for:

carrying out a computation on at least some of the forces, among which:

a first force determined by the device as a force developed by the muscle in response to a first electrostimulation generated by the apparatus at a first frequency of the range of frequencies, and a second force determined by the device as a force developed by the muscle in response to a second electrostimulation generated by the apparatus at a second frequency of the range of frequencies, the first frequency being lower than the second frequency and differing from at least 10% of the latter;

determining the muscle fatigue based on this computation.

Such computation and determination of the muscle fatigue can be performed as described in the previous embodiments, those applying mutatis mutandis to this embodiment of the system (more specifically, the logical unit abilities and/or configuration).

According to an embodiment of the system, the device comprises at least a strain gauge or a dynamometer for directly measuring the force developed by the muscle in response to an electrostimulation generated by the apparatus. Advantageously, the device allows then for a determination of the forces directly, by measuring directly these forces (in Newton) by means of an appropriate instrument and not by intermediate or indirect measures and/or observations nor deduction or estimation inducing a higher risk of error in the forces determination.

According to an embodiment of the system adapted for a muscle of a lower limb of a human as being the muscle, the device is itself a new and dedicated device for determining any force developed by the muscle in response to an electrostimulation generated by the apparatus. This device was already partially described. It comprises:
- a seat for receiving the human in a seated position, and adapted for being positioned on a horizontal support;
- a leg support element mechanically coupled to the seat, and adapted for receiving at least part of a leg of the lower limb; and
- an instrument for measuring a force developed by the muscle at level of the leg support element, in response to an electrostimulation generated by the apparatus.

The device is configured for remaining substantially stationary with respect to the horizontal support when forces are developed by the muscle at level of the leg support element, in response to the electrostimulations generated by the apparatus at the different frequencies, thanks to a weight of the human exerted at level of the seat.

Advantages of this embodiment of the system were previously discussed. This device is designed to be used without a supervising operator and has a stable and rigid structure so that the forces measurements are precise and reproducible. In particular, the device is simple and light. The device preferably does not comprise back nor leg associated with the seat, so that the seat is substantially planar and can be positioned on any horizontal support such as a table or another seat. The device is then easily transportable and allows forces measurements to be made without the need for additional equipment or structure, wherever the human is. In particular, the human has not to go in a particular medical or sport center for determining the muscle fatigue. The leg support element allows to maintain the part of the leg in position, ensuring precise and reproducible measurements of the force. The leg support element preferably comprises a semi-cylindrical hollow portion for conforming to the curvature of the part of a leg while laterally immobilizing this part of the leg. The leg support element can also comprise a strap for better immobilizing the part of the leg. The instrument consists preferentially in a strain gauge or a dynamometer that can be arranged in the device for working either in traction or in compression, so that reproducible, direct and precise measurements of the forces can be performed.

Preferably, the leg support element of the device is (mechanically) coupled to the seat by a mechanical arm or a mechanical frame. Preferably, the latter comprises a connecting member to the instrument either at level of the seat or at level of the leg support element. Advantageously, the structure of the device is then very simple and light. The arm or the frame can have a simple form, for example a projected form of "I", "L", "T", "U", "S" or "Z" in at least one plane orthogonal to the seat, and preferably comprising at least a high extremity coupled with (or fixed to) the seat, and at least a low extremity coupled with (or fixed to) the leg support element.

Optionally, the device also comprises at least a position adjustment element for modifying at least one among:
- a position and/or an orientation of the mechanical arm or the mechanical frame with respect to the seat,
- a position and/or an orientation of the leg support element with respect to the mechanical arm or the mechanical frame.

Such position adjustment element can comprise any mechanical element well known by a person skilled in the art such as a screw, a bolt, a pin, a spring, etc. preferably configured for cooperating with the mechanical arm or frame, for example, within cavities. Preferably, when the mechanical arm or frame is a mechanical arm of a simple form, it comprises such a position adjustment element for orienting the leg support element in one of two opposite senses along a direction (or line) perpendicular to the mechanical arm, one of these senses being adapted for orienting the leg support element adequately for receiving the part of the leg of the human right lower limb, and the other of these senses being adapted for orienting the leg support element adequately for receiving the part of the leg of the human left lower limb. When the mechanical arm or frame is a frame, it preferably comprises such a position adjustment element for positioning the leg support element along a side of the frame adequately for receiving the part of the leg of the human right or left lower limb. The structure of the device is then simple while being adapted to the lower limb to which belongs the muscle of which the muscle fatigue has to be determined.

More specifically, the device of the system consists preferably only in the seat, the leg support element, the instrument, the mechanical arm or the mechanical frame, and any position adjustment element if may comprise. It is then reduced to a very simple and practical form, while allowing to implement step (ii) of the determination method in a very satisfactory way for determining the muscle fatigue.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this disclosed subject matter will become more readily appreciated as the same become better understood by reference to the following detailed description, when taken in conjunction with the accompanying drawings, wherein.

The drawings in the figures are not scaled. Similar elements can be assigned by similar references in the figures. In the framework of the present document, identical or analogous elements may have the same references. The presence of reference numbers in the drawings cannot be considered to be limiting, in particular if these numbers are indicated in the claims.

DETAILED DESCRIPTION

Description of embodiments of the disclosed subject matter are hereafter described with references to figures, but the disclosed subject matter is not limited by these references. In particular, the drawings or figures described below are only schematic and are not limiting in any way.

Figure 1:
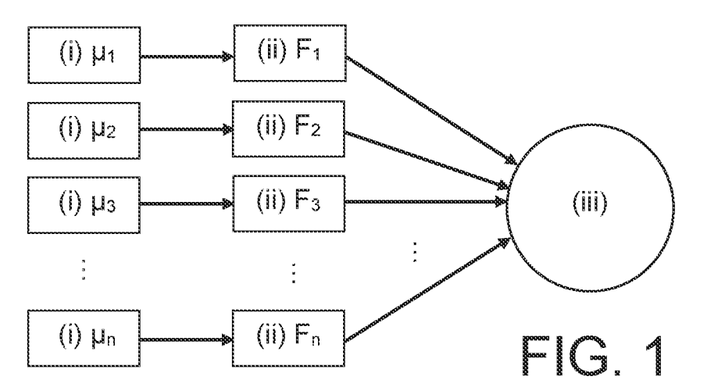
FIG. 1 shows a flow chart of the determination method according to an embodiment of the disclosed subject matter.

As illustrated in FIG. 1, the muscle fatigue determination method of the disclosed subject matter proposes to shortly electrostimulate the muscle at at least two different frequencies $\mu_1, \mu_2, \mu_3, \ldots, \mu_n$, for a number of electrostimulations $n \geq 2$, to determine, preferably to measure, the forces $F_1, F_2, F_3, \ldots, F_n$ developed by the muscle in response to each of the electrostimulations respectively at each frequencies $\mu_1, \mu_2, \mu_3, \ldots, \mu_n$, and to determine a muscle fatigue of the muscle based on the so determined forces $F_1, F_2, F_3, \ldots, F_n$. Such a determination can be performed for example by ratio computation of two forces and/or discrete integral computation, and comparison of at least one of these computations to at least one expected value, as previously explained.

FIG. 2 illustrates graphs of the force developed by the muscle in response to the electrostimulations as a function of the frequency. The force is read on the vertical axis 82 (in Newton), and the frequency is read on the horizontal axis 81 (in Hertz). The curve 61 corresponds to the graph of a theoretical expected function F expressing a force developed by a non-fatigued muscle in response to such electrostimulations as a function of the electrostimulation frequencies. The curve 62 represents a continuous and regular extension of dots cloud corresponding to the points $(\mu_1, F_1), (\mu_2, F_2), (\mu_3, F_3), \ldots, (\mu_n, F_n)$ as measured for a fatigued muscle. It is noticed that the space between the two curves 61 and 62 is greater for low frequencies (e.g. between 10 and 40 Hz), than for high frequencies (e.g. greater than 90 Hz). This space corresponds to differences 71 and 72 between measured forces for the muscle and expected forces from function F for a non-fatigued muscle respectively at low and high frequencies. In particular, the difference 72 is so small that it can be assumed that the two curves 61 and 62 are substantially the same for high frequencies. If it is assumed that the ratio F(20)/F(100) is known to be about 65%, it is then sufficient to measure the forces $F_1$ and $F_2$ developed by the muscle in response to electrostimulations at $\mu_1$=20 Hz and $\mu_2$=100 Hz respectively for determining the muscle fatigue, advantageously without the need for knowing a specific human dependent curve for the same muscle but non-fatigued. Indeed, as $F_2$ corresponds substantially to F(100), the measure of $F_2$ corresponds in some sense to a reference measure while the measure of $F_1$ allows to highlight a divergence with expected value in term of ratio to $F_2$. In particular, when the ratio $F_1/F_2$ differs significantly from 65%, a muscle fatigue is deemed to be determined according to the method and can be quantified. This value of about 65% for the ratio is indicative and not limitative. Other values such as about 60%, or about 70% or about 80% can be convenient depending on the considered function F.

Figure 3:
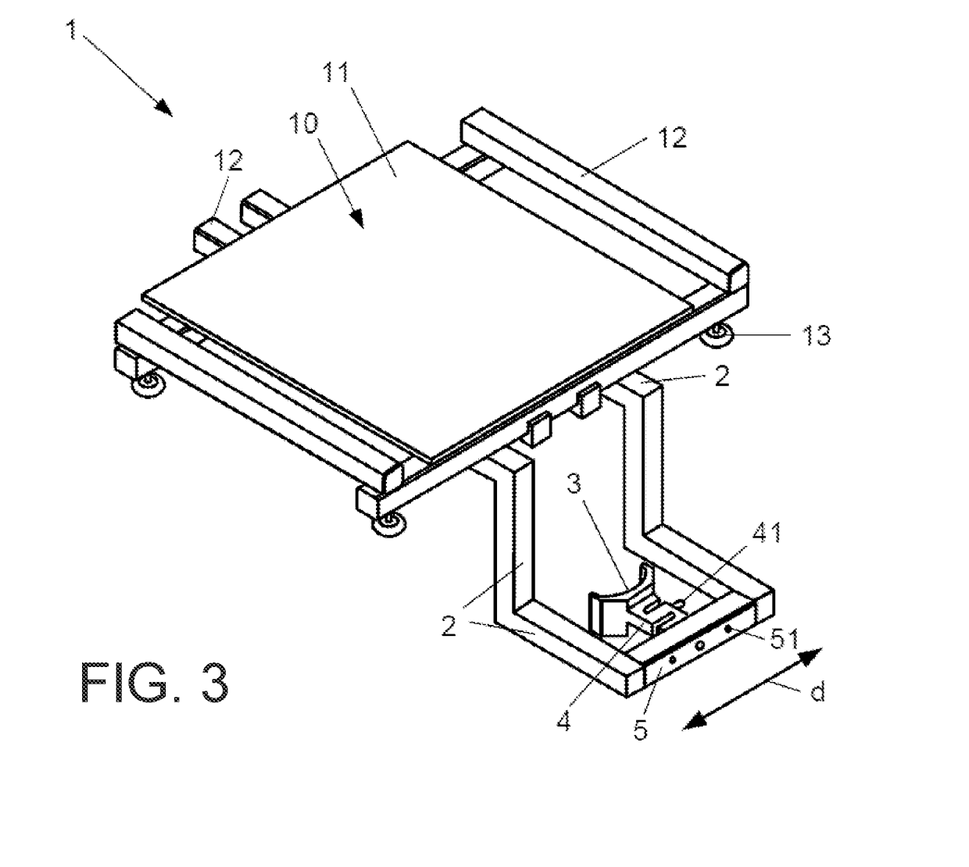
FIG. 3 shows a device of a system for determining a muscle fatigue of a muscle according to an embodiment of the disclosed subject matter.

An advantageous device 1 for measuring the forces $F_1, F_2, F_3, \ldots, F_n$ for a lower limb muscle is illustrated in FIG. 3. It is part of the muscle fatigue determination system according to various embodiments of the disclosed subject matter. The device 1 comprises a seat 10 comprising a smooth portion 11 for receiving the human in a seated position, a rigidity frame 12 for the smooth portion 11, and positioning lower members 13 for removable positioning the seat on a horizontal support. The rigidity frame 12 contribute to the rigidity of the seat, in particular at level of the smooth portion 11 which can be made of a flexible and/or padded material for the human comfort. The positioning lower members 13 can be adjustable in height from 0 to 1/20 meter below the smooth portion 11 for improving the stability of the seat 10 on the horizontal support. They can be suction cups. They can have protected extremities. They are not arranged for being placed on a ground because another part of the device 1 extend much lower than them. The device 1 comprises a leg support element 3 fixed to the seat 10 by means of a mechanical frame 2 as illustrated. The leg support element 3 includes a semi-cylindrical hollow portion for receiving and at least partially immobilizing a lower part of the lower limb leg. It integrates an instrument 4 for measuring a force developed by the muscle at level of the leg support element 3, in particular in response to the electrostimulations. The mechanical frame 2 comprises a connecting member 5 to the instrument 4 at level of the leg support element. In particular, in the illustrated configuration of FIG. 3, the instrument 4 is a strain gauge fixed along a first direction in sandwich between the leg support element 3 and the connecting member 5. The strain gauge comprises a connecting extremity 41 for connecting the device 1 with a non-represented logical unit of the determination system of the disclosed subject matter. The latter is configured for determining a muscle fatigue on basis of at least some of the forces $F_1, F_2, F_3, \ldots, F_n$ determined by the device 1 in response to the electrostimulations at each of the frequencies $\mu_1, \mu_2, \mu_3, \ldots, \mu_n$. The connecting member 5 also comprises a position adjustment element 51 for changing the position the leg support element 3 and the instrument 4 with respect to the mechanical frame 2, along a second direction d which is perpendicular to the above-mentioned first direction.

In other words, the disclosed subject matter relates to a determination method of a muscle fatigue based on information arising from forces developed by the muscle in response to electrostimulations of the latter at different frequencies. The disclosed subject matter also relates to a system for implementing the method.

The present disclosure has been described in relation to the specific embodiments which have a value that is purely illustrative and should not be considered to be limiting. The skilled person will notice that the disclosed subject matter is not limited to the examples that are illustrated and/or described here above. The disclosed subject matter comprises each of the new technical characteristics described in the present document, and their combinations.

While illustrative embodiments have been illustrated and described, it will be appreciated that various changes can be made therein without departing from the spirit and scope of the disclosed subject matter.

The invention claimed is:

1. A method of determining a muscle fatigue of a muscle, comprising the steps of:
   (i) generating electrostimulation charges at different frequencies by a device, wherein the device is adapted to provide the electrostimulation charges to the muscle;
   (ii) determining forces developed by the muscle in response to the electrostimulations of step (i); and
   (iii) determining a muscle fatigue on basis of the forces determined at step (ii),
   wherein:
   the frequencies comprise a minimal frequency smaller than 50 Hz;
   the frequencies comprise a family of frequencies smaller than 200 Hz and integer multiple of the minimal frequency; and
   step (iii) comprises:
      a computation of a discrete integral of a function associating, to each frequency of the family, a force determined at step (ii) developed by the muscle in response to the electrostimulation of step (i) at this frequency; and
      a determination of the muscle fatigue based on the computed discrete integral.

2. The method according to claim 1, wherein the frequencies of step (i) are between 0 and 1000 Hz.

3. The method according to claim 1, wherein:
   the frequencies of step (i) comprise a first frequency, and a second frequency greater than the first frequency, the first frequency differing from at least 10% of the second frequency; and the forces comprise a first force developed by the muscle in response to the electrostimulation of step (i) at the first frequency, and a second force developed by the muscle in response to the electrostimulation of step (i) at the second frequency.

4. The method according to claim 3, wherein the first frequency is between 0 and 50 Hz and/or the second frequency is between 50 and 200 Hz.

5. The method according to claim 4, wherein the first frequency is 20 Hz and/or the second frequency is 100 Hz.

6. The method according to claim 1, wherein step (iii) comprises a comparison of the forces determined at step (ii), and a determination of the muscle fatigue based on this comparison of the forces.

7. The method according to claim 3, wherein step (iii) comprises a computation of a ratio of the first force to the second force, a comparison of the computed ratio to a threshold, and a determination of the muscle fatigue based on this comparison of the computed ratio to the threshold.

8. Determination method according to claim 7, the threshold being defined by $F(\mu)/F(\mu')$, wherein:

F is a human independent increasing regular function expressing a force developed by a non-fatigued muscle in response to an electrostimulation as a function of a frequency of this electrostimulation; and $\mu$ and $\mu'$ are respectively the first and the second frequencies.

9. The method according to claim 7, wherein:
the first frequency is between 10 and 40 Hz;
the second frequency is between 90 and 120 Hz; and
the threshold is between 40 and 90%.

10. The method according to claim 1, wherein the forces are determined in steps (ii) by direct force measurements by means of a strain gauge or a dynamometer.

11. The method according to claim 1, wherein the muscle fatigue determined at step (iii) consists in a long-lasting peripheral muscle fatigue.

12. The method according to claim 1, wherein the device is adapted to provide the electrostimulation charges to at least a portion of a muscle of a lower limb of a human.

13. The method according to claim 12, comprising, before step (i), the steps of:
(a) providing the device, the device comprising:
a seat for receiving the human in a seated position and adapted for being positioned on a horizontal support;
a leg support element mechanically coupled to the seat and adapted for receiving at least part of a leg of the lower limb; and
an instrument for measuring the forces at level of the leg support element; and
(b) positioning the seat on a horizontal support,
wherein the forces are determined at step (ii) by means of the instrument,
and wherein the device remains substantially stationary with respect to the horizontal support during an execution of steps (i) and (ii) based on a weight of the human exerted at level of the seat.

14. The method according to claim 13, wherein the device is configured to support the human such that:
a foot of the lower limb hangs in the air;
a whole thigh of the lower limb lies on the seat; and
a back of a knee of the lower limb is in contact with a lateral side of the seat.

* * * * *